United States Patent [19]

Salmond

[11] 4,001,096

[45] Jan. 4, 1977

[54] PROCESS FOR PREPARING 25-HYDROXYCHOLECALCIFEROL INTERMEDIATES

[75] Inventor: William G. Salmond, Kalamazoo, Mich.

[73] Assignee: The Upjohn Company, Kalamazoo, Mich.

[22] Filed: Feb. 21, 1975

[21] Appl. No.: 551,698

[52] U.S. Cl. .............................. 204/158 R; 204/159
[51] Int. Cl.² ................... B01J 1/10; C07G 13/00; C07J 9/00
[58] Field of Search ....................... 204/158 R, 159; 260/397.2

[56] References Cited

UNITED STATES PATENTS 3,661,939   5/1972   Toyoda et al. .................... 204/159

OTHER PUBLICATIONS

Campbell et al., Steroids, vol. 13(1969) pp. 567–577.

*Primary Examiner*—Howard S. Williams
*Attorney, Agent, or Firm*—Martin B. Barancik; Roman Saliwanchik

[57] ABSTRACT

A method for preparing 9$\beta$, 10$\alpha$-cholesta-5,7-diene-3$\beta$,25 diol and 25-hydroxyprevitamin $D_3$ by irradiation.

5 Claims, No Drawings

PROCESS FOR PREPARING 25-HYDROXYCHOLECALCIFEROL INTERMEDIATES

BRIEF DESCRIPTION OF THE PRIOR ART

25-Hydroxycholecalciferol is a newly discovered metabolite of vitamin $D_3$. A number of methods are available for preparing 25-hydroxycholecalciferol. Among these methods is the thermal rearrangement of the 25-hydroxy previtamin $D_3$ schematic figure below, to 25-hydroxycholecalciferol, Campbell, Squires and Babcock, Steroids, 13, 567 (1969).

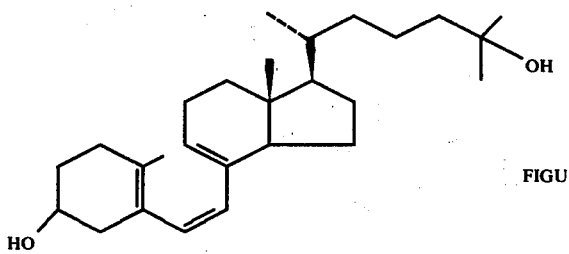

FIGURE I

The previtamin can be prepared by the irradiation of cholesta-5,7-diene-3β,25-diol, as stated in the previous reference.

BRIEF SUMMARY OF THE INVENTION

It has now been found that the novel compound 9β,10α-cholesta-5,7-diene-3β,25-diol is prepared by the irradiation of cholesta-5,7-diene-3β,25-diol. This new compound can be isolated in crystalline form from the reaction mixture. Thereafter, the 9β,10α compound can be irradiated to form 25-hydroxy previtamin $D_3$. Therefore, the methods of this invention result in increased yields of 25-hydroxycholecalciferol.

In accordance with this invention, a method for producing 9β,10α-cholesta-5,7-diene-3β,25-diol is disclosed, which comprises irradiating cholesta-5,7-diene-3β,25-diol. The crystalline product can be recovered from the reaction mixture.

A further aspect of the invention is the method of producing the 25-hydroxyprevitamin $D_3$ which comprises irradiating 9β,10α-cholesta-5,7-diene-3β-25-diol.

A still further aspect of the invention is the novel compound 9β,10α-cholesta-5,7-diene-3β-25-diol, schematic FIG. II below:

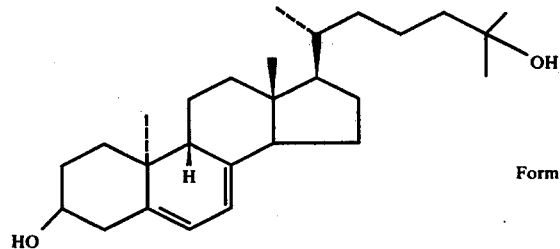

Formula II

DETAILED DESCRIPTION OF THE INVENTION

The irradiation of cholesta-5,7-diene-3β,25-diol is carried out by conventional, art recognized methods as used in the cited reference. It is preferred to use radiation of wavelength greater than about 270–280 mμ to effectuate the transformation. The reaction product 25-hydroxy previtamin $D_3$ is in photochemical equilibrium with the starting material and is also in equilibrium with the 9β,10α-cholesta-5,7-diene-3β-25-diol and 25-hydroxy tachysterol₃, a further reaction product. The use of radiation of wavelength greater than 270–280mμ reduces the quantity of 25-hydroxy tachysterol₃ side product and increases the quantity of 9β,10α-cholesta-5,7-diene-3β,25-diol produced.

A convenient source of radiation is a medium pressure mercury lamp. In order to achieve radiation of the preferred wavelength, this radiation can be passed through Corex glass of a thickness of 2 mm. Corex glass is obtained from Corning Company.

The time of radiation is directly related to the lamp intensity. The reaction course can be followed by analysis of the reaction mixture by gas-liquid chromatographic means. When an appropriate concentration level of the desired compound is reached, the reaction is terminated. The weaker the intensity of radiation, the longer the reaction time.

The temperature of the irradiated solution is not unduly significant. Temperatures of from about −10° to about 20° C. can be readily employed. It is preferable to maintain a range of from about 0° to about 10° C. to limit the production of the vitamin.

The cholesta-5,7-diene-3β,25-diol is irradiated in solution. Any organic solvent which does not interfere detrimentally with the course of reaction can be employed. Typical of such solvents are dialkylethers of two to eight carbon atoms, inclusive, and cyclic ethers of four to eight carbon atoms, inclusive. Illustrative examples of these solvents are diethylether, dibutylether, ethylpropylether, tetrahydrofuran, 1,4-dioxane and like molecules.

The irradiation of the solution can be carried out as disclosed above, however, it is preferred to have the solution essentially oxygen free. It is well known that free oxygen contributes to the increase of undesirable side reactions. Oxygen can be removed from the solution by standard methods such as a nitrogen purge.

The conversion of 9β,10α-cholesta-5,7-diene-3β,25-diol to the 25-hydroxyprevitamin $D_3$ by irradiation is carried out in the same manner as the irradiation of cholesta-5,7-diene-3β,25-diol. Radiation above 270–280 mμ is preferred. The irradiation is carried out in a solution which is preferably essentially free of oxygen. The same type of solvents disclosed previously can also be used for this reaction. The reaction temperature is maintained at the same range as the previous irradiation.

The following specific examples serve to illustrate the scope of the invention. They are not intended to narrow the invention.

EXAMPLE 1

9β,10α-cholesta-5,7-diene-3β,25-diol 25.0 g. of cholesta-5,7-diene-3β,25-diol dissolved in 4.7 l. of dry oxygen-free tetrahydrofuran is irradiated for nineteen hours with a medium pressure mercury lamp, the light of which is filtered through Corex glass of 2 mm. thickness. The temperature is kept below 15° C. throughout this period. The solution is then evaporated to dryness at a temperature of less than 35° C. The residue is slurried with 75 ml. ethyl acetate and 130 ml. of Skellysolve B and cooled to 0° C. The solid which is starting material is filtered and the filtrate is now evaporated. The residual oil is dissolved in 200 ml. benzene and stirred at 70° C. for 16 hours under a blanket of nitrogen. The solution is then evaporated and the residue dissolved in aqueous acetone from which 25-hydroxycholecalciferol hydrate crystallizes. This is filtered off and the filtrate evaporated to dryness. The residue is chromatographed on Florisil and eluted with a mixture of ethyl acetate and Skellysolve B. There is obtained a first fraction from which more 25-hydroxycholecalciferol hydrate is obtained and then a fraction from which 9β,10α-cholesta-5,7-diene-3β,25-diol is obtained as white crystals from acetonitrile, M.P. 122°–125° C.

NMR (CDCl$_3$):

δ0.63s (3H); 0.75s (3H); 1.20s (6H);
4.10m (1H); 5.57 AB J=ca 6H$_z$ (2H);
α$_D$ (CHCl$_3$): +185°

EXAMPLE 2

Preparation of 25-hydroxyprevitamin D$_3$

9β,10α-cholesta-5,7-diene-3β,25-diol (5.0 g.) in 1 l. dry oxygen-free tetrahydrofuran, is irradiated in a like fashion to that described in Example 1. Working up in an analogous fashion to Example 1, some cholesta-5,7-diene-3β,25-diol is initially isolated. After a thermal treatment of the materials contained in the filtrate, similar to that of Example 1, 25-hydroxycholecalciferol is isolated.

I claim:

1. A method for preparing 9β,10α-cholesta-5,7-diene-3β,25-diol which comprises irradiating cholesta-5,7-diene-3β,25-diol and recovering crystalline 9β,10α-cholesta-5,7-diene-3β,25-diol from the reaction mixture.

2. A method in accordance with claim 1 wherein radiation of wavelength greater than 270–280 mμ is employed.

3. A method in accordance with claim 1 wherein the crystalline compound is isolated by chromatographic means.

4. A method for preparing 25-hydroxyprevitamin D$_3$

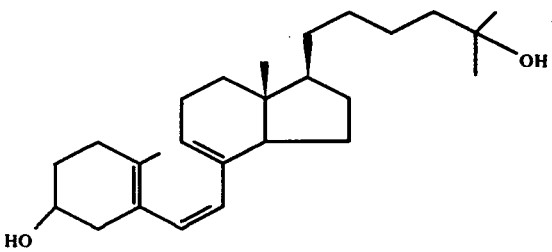

which comprises
 a. dissolving crystalline 9β,10α-cholesta-5,7-diene-3β,25-diol in an organic solvent,
 b. irradiating the solution of 9β,10α-cholesta-5,7-diene-3β-25-diol.

5. A method in accordance with claim 4 wherein radiation of wavelength greater than 270–280 mμ is employed.

* * * * *